(12) United States Patent
Lu et al.

(10) Patent No.: US 10,882,825 B2
(45) Date of Patent: Jan. 5, 2021

(54) NON-SOLVATED CRYSTAL, PREPARATION METHOD AND APPLICATION THEREOF

(71) Applicant: SHENZHEN CHIPSCREEN BIOSCIENCES CO., LTD., Guangdong (CN)

(72) Inventors: Xianping Lu, Guangdong (CN); Zhibin Li, Guangdong (CN)

(73) Assignee: SHENZHEN CHIPSCREEN BIOSCIENCES CO., LTD., Guangdong (CN)

( * ) Notice: Subject to any disclaimer, the term of this patent is extended or adjusted under 35 U.S.C. 154(b) by 0 days.

(21) Appl. No.: 16/337,389

(22) PCT Filed: Sep. 27, 2017

(86) PCT No.: PCT/CN2017/103620
§ 371 (c)(1),
(2) Date: Mar. 27, 2019

(87) PCT Pub. No.: WO2018/059429
PCT Pub. Date: Apr. 5, 2018

(65) Prior Publication Data
US 2020/0031774 A1 Jan. 30, 2020

(30) Foreign Application Priority Data
Sep. 27, 2016 (CN) .......................... 2016 1 0856945

(51) Int. Cl.
*C07D 215/20* (2006.01)
*A61K 31/47* (2006.01)
*C07D 215/233* (2006.01)
*A61K 9/20* (2006.01)
*A61K 9/48* (2006.01)

(52) U.S. Cl.
CPC ........ *C07D 215/233* (2013.01); *A61K 9/2009* (2013.01); *A61K 9/2027* (2013.01); *A61K 9/2054* (2013.01); *A61K 9/2059* (2013.01); *A61K 9/4858* (2013.01); *A61K 9/4866* (2013.01); *C07B 2200/13* (2013.01)

(58) Field of Classification Search
CPC .............................. C07D 215/20; A61K 31/47
USPC .......................................... 546/153; 514/312
See application file for complete search history.

(56) References Cited

U.S. PATENT DOCUMENTS

2010/0298358 A1    11/2010    Lu et al.

FOREIGN PATENT DOCUMENTS

| CN | 101906076 A | 12/2010 |
| EP | 2439195 A1 | 4/2012 |
| RU | 2497809 C2 | 11/2013 |

OTHER PUBLICATIONS

Sherry L.Morissette et al.: "High-throughput crystallization: polymorphs, salts, co-crystals and solvates of pharmaceutical solids", Advanced Drug Delivery Reviews, 2004, v.56, pp. 275-300 (section 1;3.1) (DOI:10.1016/J.ADDR.2003.10.020).
Mino R.Caira, Crystalline Polymorphism of Organic Compounds, 1998, p. 163-208 (Section 3.1).
Stout, T., Foster, P., & Matthews, D: "High-Throughput Structural Biology in Drug Discovery: Protein Kinases", Current Pharmaceutical Design, 10(10), (2004), c.1069-1082 (doi:10.2174/1381612043452695).
First Office Action dated Dec. 19, 2019 for Russian patent application No. 2019112457, 8 pages, English translation provided by Gorodissky.
International Search Report for PCT/CN2017/103620 dated Dec. 29, 2017, ISA/CN.

*Primary Examiner* — Charanjit Aulakh
(74) *Attorney, Agent, or Firm* — Yue (Robert) Xu; Apex Attorneys at Law, LLP

(57) ABSTRACT

The invention relates to non-solvated crystals A, B and C of N-(2-aminophenyl)-6-(7-methoxyquinoline-4-oxy)-1-naphthamide and preparation methods thereof. The invention also relates to pharmaceutical compositions containing the crystals, and a use of the crystals in preparation of a medicament for the treatment of a disease associated with abnormal protein kinase activity or abnormal histone deacetylase activity.

16 Claims, 10 Drawing Sheets

NON-SOLVATED CRYSTAL, PREPARATION METHOD AND APPLICATION THEREOF

CROSS REFERENCE TO RELATED APPLICATIONS

The present disclosure is the national phase of International Application No. PCT/CN2017/103620, titled "NON-SOLVATED CRYSTAL, PREPARATION METHOD AND APPLICATION THEREOF", filed on Sep. 27, 2017, which claims the priority to Chinese Patent Application No. 201610856945.2 titled "NON-SOLVATED CRYSTAL, PREPARATION METHOD AND APPLICATION THEREOF", filed on Sep. 27, 2016 with the State Intellectual Property Office of the People's Republic of China, which is incorporated herein by reference in entirety.

FIELD

The present disclosure relates to the field of medicinal chemistry, and in particular to a non-solvated crystal of N-(2-aminophenyl)-6-(7-methoxyquinoline-4-oxo)-1-naphthaleneformamide as well as preparation method and application thereof.

BACKGROUND

N-(2-aminophenyl)-6-(7-methoxyquinoline-4-oxo)-1-naphthaleneformamide is a protein kinase and histone deacetylase dual target inhibition, the chemical structure of it is shown in structural formula (I)

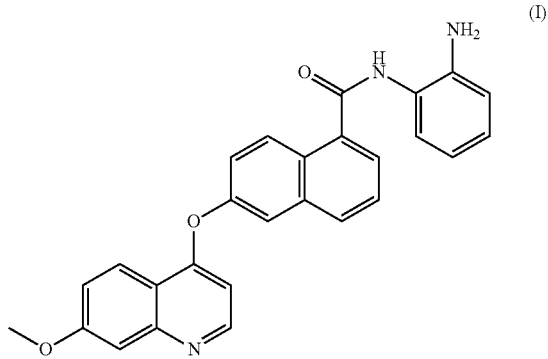 [SMILES: COc1ccc2c(Oc3ccc4c(C(=O)Nc5ccccc5N)cccc4c3)ccnc2c1]

Pharmacological activity of the compound of the formula (I) is described in Chinese patent application CN200910223861.5, which has a protein kinase inhibitory activity and a histone deacetylase inhibitory activity, and can be used for the treatment of a disease associated with abnormal protein kinase activity or abnormal histone deacetylase activity, including inflammation, autoimmune diseases, cancer, nervous system diseases and neurodegenerative diseases, cardiovascular diseases, metabolic diseases, allergies, asthma, and hormone-related diseases, and especially have excellent efficacy for treating blood cancer and solid tumors.

The present inventors prepared the compound of the formula (I) according to the method described in Example 31 of the Chinese patent application CN200910223861.5, and the X-ray powder diffraction pattern of the obtained solid is shown in FIG. 1. In fact, the solid of the compound of formula (I) prepared by this process inevitably contains N,N-dimethylformamide (DMF), which has been confirmed by its proton nuclear magnetic resonance spectrum ($^1$H NMR). The resulting solid is a solvated crystal of N,N-dimethylformamide (DMF), which contains 1.4% DMF.

Since organic solvents are potentially toxic to the drug user, it is generally not desirable to prepare crystals containing organic solvents. The International Conference of Harmonizition (ICH) specifies residual limits of various common organic solvents in pharmaceuticals. For example, the limits of N,N-dimethylformamide (DMF), chloroform, methanol, tetrahydrofuran, toluene, ethyl acetate, butyl acetate, dimethyl sulfoxide (DMSO), ethanol, and methyl isobutyl ketone are 0.088%, 0.006%, 0.3%, 0.072%, 0.089%, 0.5%, 0.5%, 0.5%, 0.5% and 0.5% respectively.

The compound of the formula (I) obtained by the method of Example 31 of the Chinese patent application CN200910223861.5 has a residual amount of DMF far exceeding the limit as prescribed by ICH. There are no methods in the art for preparing non-solvated crystals of the compounds of formula (I). Therefore, there is an urgent need to prepare non-solvated crystals of the compound of formula (I) for safe use in manufacture of a medicament.

SUMMARY

It is an object of the present disclosure to overcome the disadvantages of the prior art, and to provide a non-solvated crystal of the compound of formula (I).

The present invention provides three non-solvated crystals of the compound of formula (I).

Provided is a non-solvated crystal A of the compound of formula (I). Its X-ray powder diffraction pattern has characteristic peaks at reflection angles 2θ of about 4.42°, 6.88°, 8.78°, 9.26°, 12.74°, 13.82°, 15.78°, 18.58°, 20.86°, 22.56°, 25.72°, 27.08° and 28.72°; its infrared spectrum has characteristic absorption peaks at about 3452, 3404, 3357, 3230, 3064, 1622, 1576, 1525, 1506, 1452, 1423, 1388, 1363, 1311, 1253, 1224, 1161, 1088 and 1024 cm$^{-1}$; its differential scanning calorimetry curve has endothermic peaks at about 177.5° C., 213.1° C., and 220.8° C.; its proton nuclear magnetic resonance spectroscopy indicates that the crystal does not contain organic solvents, fully compliant with the limits for solvent residues as prescribed by ICH.

Provided is a non-solvated crystal B of the compound of formula (I). Its X-ray powder diffraction pattern has characteristic peaks at reflection angles 2θ of about 4.88°, 9.68°, 12.74°, 14.52°, 17.72°, 19.82°, 21.86°, 24.30° and 25.26°; its infrared spectrum has characteristic absorption peaks at about 3423, 3352, 3238, 3030, 1624, 1597, 1531, 1502, 1452, 1423, 1388, 1365, 1308, 1255, 1226, 1159, 1086 and 1022 cm$^{-1}$; its differential scanning calorimetry curve has an endothermic peak at about 178.6° C.; its proton nuclear magnetic resonance spectroscopy indicates that the crystal does not contain organic solvents, fully compliant with the limits for solvent residues as prescribed by ICH.

Provided is a non-solvated crystal C of the compound of formula (I). Its X-ray powder diffraction pattern has characteristic peaks at reflection angles 2θ of about 4.84°, 9.68°, 12.92°, 14.60°, 16.46°, 17.20°, 17.44°, 17.88°, 19.20°, 20.54°, 21.06°, 22.00°, 25.28° and 27.66°; its infrared spectrum has characteristic absorption peaks at about 3452, 3369, 3217, 3016, 2962, 1793, 1728, 1626, 1595, 1574, 1531, 1502, 1448, 1429, 1388, 1311, 1252, 1224, 1159 and 1020 cm$^{-1}$; its differential scanning calorimetry curve has endothermic peaks at about 196.3° C. and 221.0° C.; its proton nuclear magnetic resonance spectroscopy indicates that the crystal does not contain organic solvents, fully compliant with the limits for solvent residues as prescribed by ICH.

Thus, in a first aspect of the present disclosure, it is provided a non-solvated crystal of N-(2-aminophenyl)-6-(7-methoxyquinoline-4-oxo)-1-naphthaleneformamide.

In one embodiment, the non-solvated crystal comprises non-solvated crystals A, B and C of N-(2-aminophenyl)-6-(7-methoxyquinoline-4-oxo)-1-naphthaleneformamide.

In one embodiment, the non-solvated crystal A is characterized in that its X-ray powder diffraction pattern has characteristic peaks at reflection angles (2θ) of 6.88°, 9.26°, 12.74°, 13.82°, 18.58°, 20.86° and 25.72°; preferably, its X-ray powder diffraction pattern has characteristic peaks at reflection angles (2θ) of 4.42°, 6.88°, 8.78°, 9.26°, 12.74°, 13.82°, 18.58°, 20.86° and 25.72°; more preferably, its X-ray powder diffraction pattern has characteristic peaks at reflection angles (2θ) of 4.42°, 6.88°, 8.78°, 9.26°, 12.74°, 13.82°, 15.78°, 18.58°, 20.86°, 22.56°, 25.72°, 27.08° and 28.72°; most preferably, its X-ray powder diffraction pattern is shown in FIG. 2.

In one embodiment, the infrared spectrum of the non-solvated crystal A has characteristic absorption peaks at 3452, 3404, 3357, 3230, 3064, 1622, 1576, 1525, 1506, 1452, 1423, 1388, 1363, 1311, 1253, 1224, 1161, 1088 and 1024 $cm^{-1}$, and is preferably shown in FIG. 3; its differential scanning calorimetry curve has endothermic peaks at 177.5° C., 213.1° C., and 220.8° C., and is preferably shown in FIG. 4.

In one embodiment, the non-solvated crystal B is characterized in that its X-ray powder diffraction pattern has characteristic peaks at reflection angles (2θ) of 4.88°, 9.68°, 12.74°, 14.52°, 17.72°, 24.30° and 25.26°; preferably, its X-ray powder diffraction pattern has characteristic peaks at reflection angles (2θ) of 4.88°, 9.68°, 12.74°, 14.52°, 17.72°, 19.82°, 21.86°, 24.30° and 25.26°; more preferably, its X-ray powder diffraction pattern is shown in FIG. 5.

In one embodiment, the infrared spectrum of the non-solvated crystal B has characteristic absorption peaks at 3423, 3352, 3238, 3030, 1624, 1597, 1531, 1502, 1452, 1423, 1388, 1365, 1308, 1255, 1226, 1159, 1086 and 1022 $cm^{-1}$, and is preferably shown in FIG. 6; its differential scanning calorimetry curve has an endothermic peak at 178.6° C., and is preferably shown in FIG. 7.

In one embodiment, the non-solvated crystal C is characterized in that its X-ray powder diffraction pattern has characteristic peaks at reflection angles (2θ) of 4.84°, 9.68°, 12.92°, 14.60°, 16.46°, 17.44°, 22.00 and 25.28°; preferably, its X-ray powder diffraction pattern has characteristic peaks at reflection angles (2θ) of 4.84°, 9.68°, 12.92°, 14.60°, 16.46°, 17.44°, 17.88°, 22.00°, 25.28° and 27.66°; more preferably, its X-ray powder diffraction pattern has characteristic peaks at reflection angles (2θ) of 4.84°, 9.68°, 12.92°, 14.60°, 16.46°, 17.20°, 17.44°, 17.88°, 19.20°, 20.54°, 21.06°, 22.00°, 25.28° and 27.66°; most preferably, its X-ray powder diffraction pattern is shown in FIG. 8.

In one embodiment, the infrared spectrum of the non-solvated crystal C has characteristic absorption peaks at 3452, 3369, 3217, 3016, 2962, 1793, 1728, 1626, 1595, 1574, 1531, 1502, 1448, 1429, 1388, 1311, 1252, 1224, 1159 and 1020 $cm^{-1}$, and is preferably shown in FIG. 9; its differential scanning calorimetry curve has endothermic peaks at 196.3° C. and 221.0° C., and is preferably shown in FIG. 10.

The invention further provides a method for preparing the three non-solvated crystals of the compound of formula (I).

The method for preparing the non-solvated crystal A of the compound of formula (I) comprises the steps of: adding N-(2-aminophenyl)-6-(7-methoxyquinoline-4-oxo)-1-naphthaleneformamide to methanol, heating at 65° C. until dissolved and cooling at 0° C. to precipitate. In a preferred embodiment, the method for preparing the non-solvated crystal A comprises the steps of: adding N-(2-aminophenyl)-6-(7-methoxyquinoline-4-oxo)-1-naphthaleneformamide to methanol, heating at 65° C. until dissolved and cooling at 0° C. to precipitate, filtering to collect solid, and drying it under vacuum at 80° C. for 12 hours to obtain the product.

The method for preparing the non-solvated crystal B of the compound of formula (I) comprises the steps of: adding N-(2-aminophenyl)-6-(7-methoxyquinoline-4-oxo)-1-naphthaleneformamide to acetonitrile, heating at 80° C. until dissolved and cooling at 0° C. to precipitate. In a preferred embodiment, the method for preparing the non-solvated crystal B comprises the steps of: adding N-(2-aminophenyl)-6-(7-methoxyquinoline-4-oxo)-1-naphthaleneformamide to acetonitrile, heating at 80° C. until dissolved and cooling at 0° C. to precipitate, filtering to collect solid, and drying it under vacuum at 80° C. for 12 hours to obtain the product.

The method for preparing the non-solvated crystal C of the compound of formula (I) comprises the steps of: adding N-(2-aminophenyl)-6-(7-methoxyquinoline-4-oxo)-1-naphthaleneformamide to dimethyl sulfoxide, stirring at room temperature until dissolved, and adding dropwise the resulting solution to water under stirring, and filtering to collect solid. In a preferred embodiment, the method for preparing the non-solvated crystal C comprises the steps of: adding N-(2-aminophenyl)-6-(7-methoxyquinoline-4-oxo)-1-naphthaleneformamide to dimethyl sulfoxide, stirring at room temperature until dissolved, and adding dropwise the resulting solution to water under stirring, and filtering to collect solid, washing it with water, and drying it under vacuum at 80° C. for 24 hours to obtain the product.

In another aspect of the present disclosure, it is provided a pharmaceutical composition comprising the non-solvated crystal of N-(2-aminophenyl)-6-(7-methoxyquinoline-4-oxo)-1-naphthaleneformamide. In one embodiment, the present disclosure provides a pharmaceutical composition for the treatment of a disease associated with abnormal protein kinase activity or abnormal histone deacetylase activity, comprising the non-solvated crystal of N-(2-aminophenyl)-6-(7-methoxyquinoline-4-oxo)-1-naphthaleneformamide, and optionally pharmaceutically acceptable excipients and/or carriers.

The pharmaceutical compositions of the present disclosure may contain any suitable pharmaceutically acceptable excipients and/or carriers. The pharmaceutical compositions of the present disclosure can be prepared by conventional techniques, such as those described in Remington: The Science and Practice of Pharmacy, 19$^{th}$ edition, 1995, which is incorporated herein by reference. The composition may be presented in conventional forms such as tablets, capsules, powders, granules, suspensions, syrups, solutions, injections, ointments, and the like. The preparations usually contain 0.5% to 70% by weight of the compound of the formula (I) and 30% to 99.5% by weight of the pharmaceutical adjuvants, preferably 1% to 65% by weight, 3% to 60% by weight, 5% to 55% by weight, 10% to 50% by weight, 20% to 40% by weight, 25% to 38% by weight, 30% to 35% by weight or 32% to 34% by weight of the compound of formula (I).

A typical composition comprises a compound of the present disclosure and an excipient or carrier. For example, the active compound is usually mixed with a carrier, or diluted by a carrier, or sealed in a carrier which may be in the form of an ampule, capsule, sachet, paper or other container. If the active compound is mixed with a carrier, or if a carrier serves as a diluent, the carrier can be a solid, semi-solid or liquid material that serves as a carrier, excipient or medium for the active compound. The active compound can be adsorbed onto a particulate solid carrier (e.g., contained in a sachet). Some examples of the suitable carriers are water, salt solutions, alcohols, polyethylene glycols, polyhydroxyethoxylated castor oil, peanut oil, olive oil, gelatin, lactose, white earth, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and glycerol diester, pentaerythritol fatty acid ester, polyoxyethylene, hydroxymethyl cellulose and polyvinylpyrrolidone. Similarly, the carrier or diluent may include any sustained release material known in the art, such as glyceryl monostearate or glyceryl distearate alone or their mixture with a wax.

In yet another aspect of the present disclosure, it is provided use of the non-solvated crystal of N-(2-aminophenyl)-6-(7-methoxyquinoline-4-oxo)-1-naphthaleneformamide in the manufacture of a medicament for the treatment of a disease associated with abnormal protein kinase activity or abnormal histone deacetylase activity. Preferably, the disease associated with abnormal protein kinase activity or abnormal histone deacetylase activity is selected from the group consisting of inflammation, autoimmune diseases, cancer, nervous system diseases and neurodegenerative diseases, cardiovascular diseases, metabolic diseases, allergies, asthma, and hormone-related diseases, and especially blood cancer and solid tumors The non-solvated crystals A, B and C of the compound of formula (I) were placed under high temperature (60° C.), high humidity (90%±5%) and intense light irradiation (4500 Lx±500 Lx) for 10 days, the three crystals remain unchanged in their original crystal forms, and the content of each crystal does not change significantly, indicating that the three crystals are all suitable for pharmaceutical manufacturing and long-term storage.

DETAILED DESCRIPTION

The contents of the present disclosure are further described below with reference to examples, but the scope of protection of the present disclosure is not limited to these examples. The percentages stated in the present disclosure are all percentages by weight unless otherwise specified. The range of values described in the specification, such as units of measure, reaction conditions, physical state of the compound, or percentage, are intended to provide an unambiguous written reference. Those skilled in the art, when practicing the patent, will still be able to obtain the desired results using temperatures, concentrations, amounts, number of carbon atoms, etc. outside of this range or different from a single value.

Test method:

Test conditions of X-ray powder diffraction: instrument: D/MAX-1200 (Rigaku, Japan); radiation source: Cu-Kα (40 kV, 40 mA).

Test conditions of infrared spectroscopy: instrument: RFX-65A (Analect, USA); KBr tableting method.

Test conditions of differential scanning calorimetry: instrument: Pyris-1-DSC (PerkinElmer, USA); heating rate: 10° C./min; nitrogen flow rate: 40 mL/min.

Test conditions of proton nuclear magnetic resonance: instrument: AV-400 (BRUKER, Germany); solvent: DMSO-$d_6$.

Test conditions of stability: high temperature (60° C.), high humidity (90%) and strong light irradiation (4500 Lx) tests are performed according to the Chinese Pharmacopoeia 2010 edition, Part II, Appendix XIX C.

Test conditions of HPLC: instrument: Dionex UltiMate3000; column: Shim-pack VP-ODS 5 μm 250 L×4.6; detector: VWD-3100, detection wavelength: 256 nm; mobile phase: methanol-water-glacial acetic acid (30:70: 0.4); flow rate: 1.0 mL/min, column temperature: 30° C.

EXAMPLE 1

Figure 1:
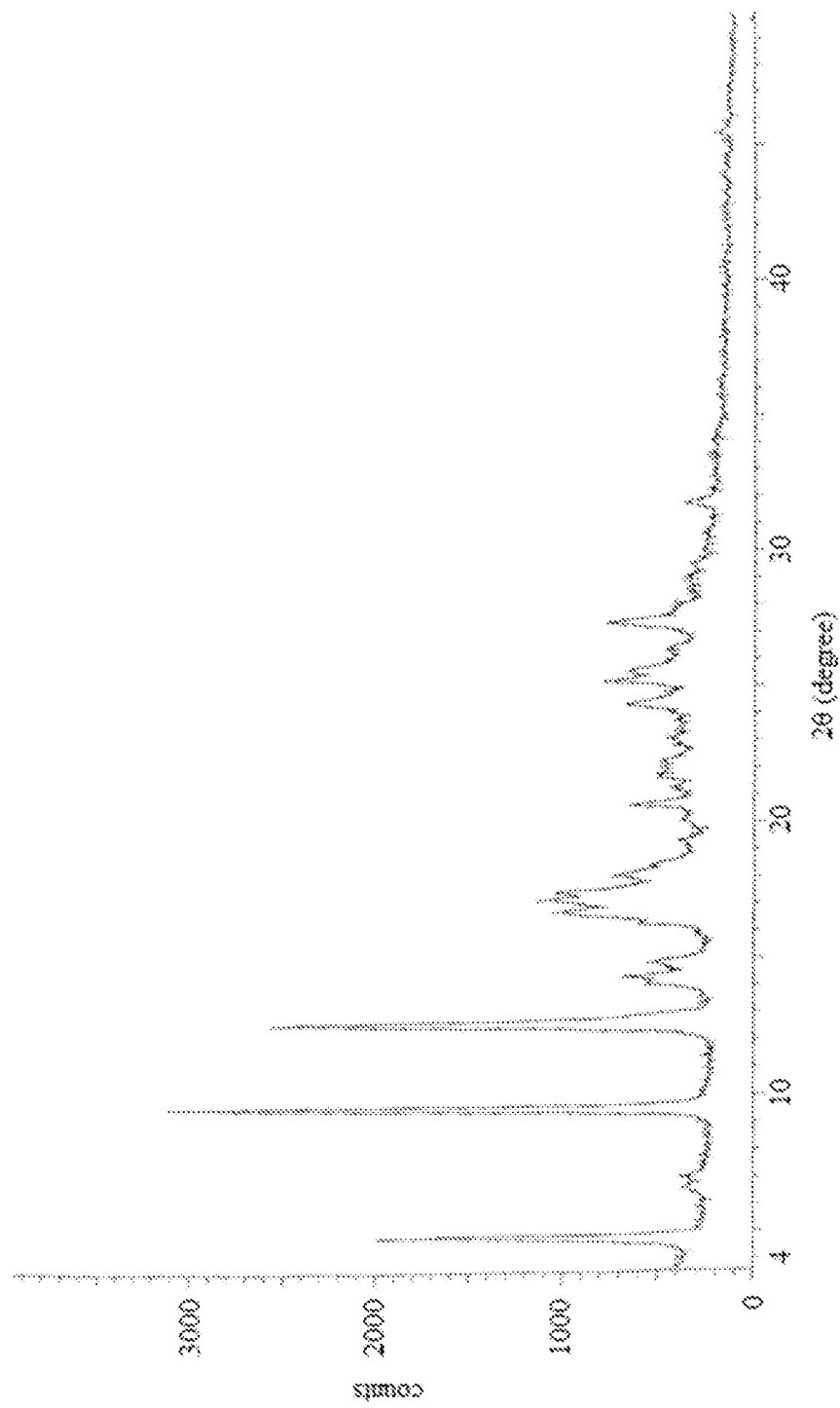
FIG. 1 is an X-ray powder diffraction pattern of the solid prepared in accordance with Example 31 of the Chinese patent application CN200910223861.5.
Figure 2:
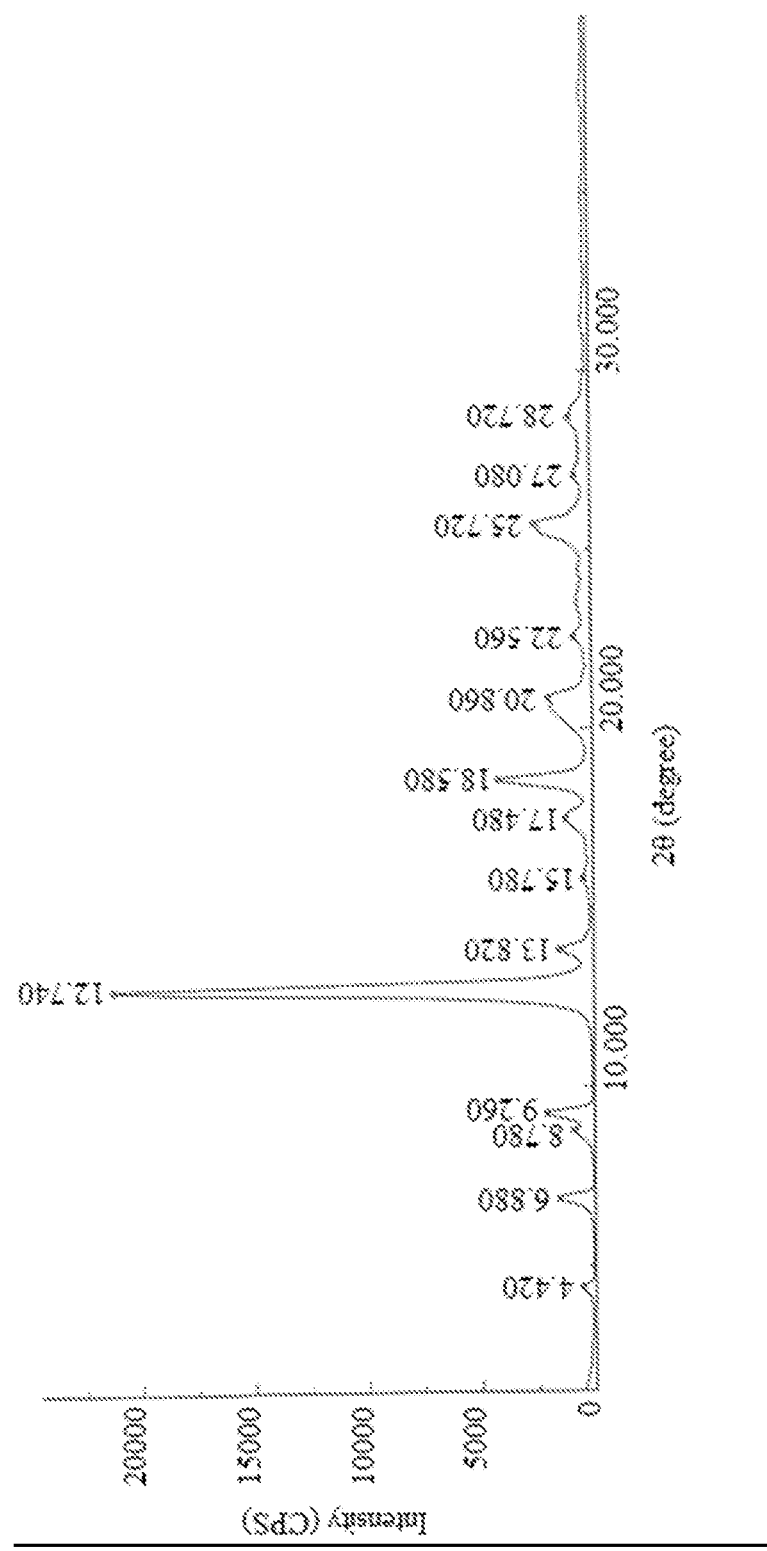
FIG. 2 is an X-ray powder diffraction pattern of the non-solvated crystal A of the compound of formula (I) prepared in accordance with Example 1 of the present disclosure.
Figure 3:
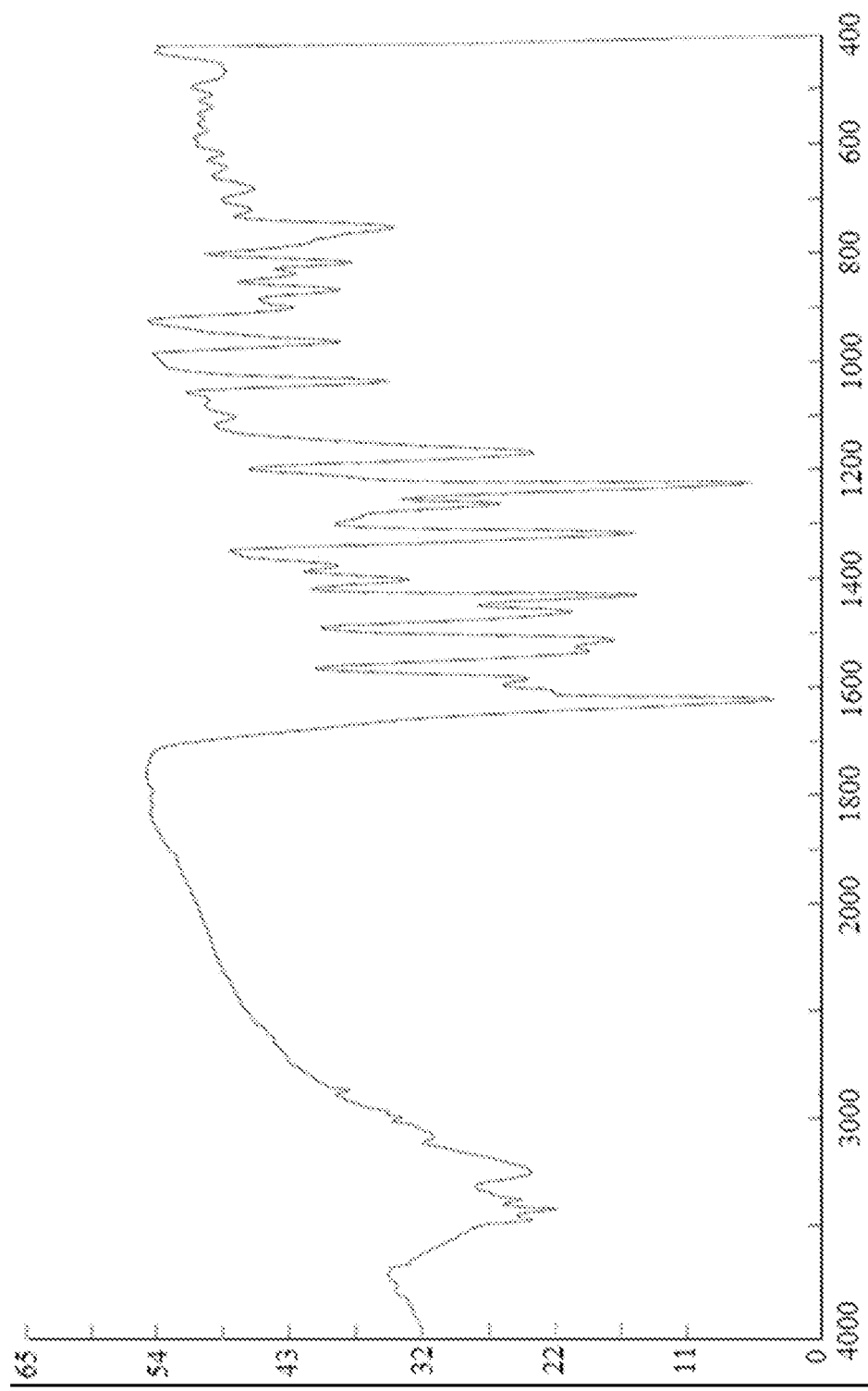
FIG. 3 is an infrared spectrum of the non-solvated crystal A of the compound of formula (I) prepared in accordance with Example 1 of the present disclosure.
Figure 4:
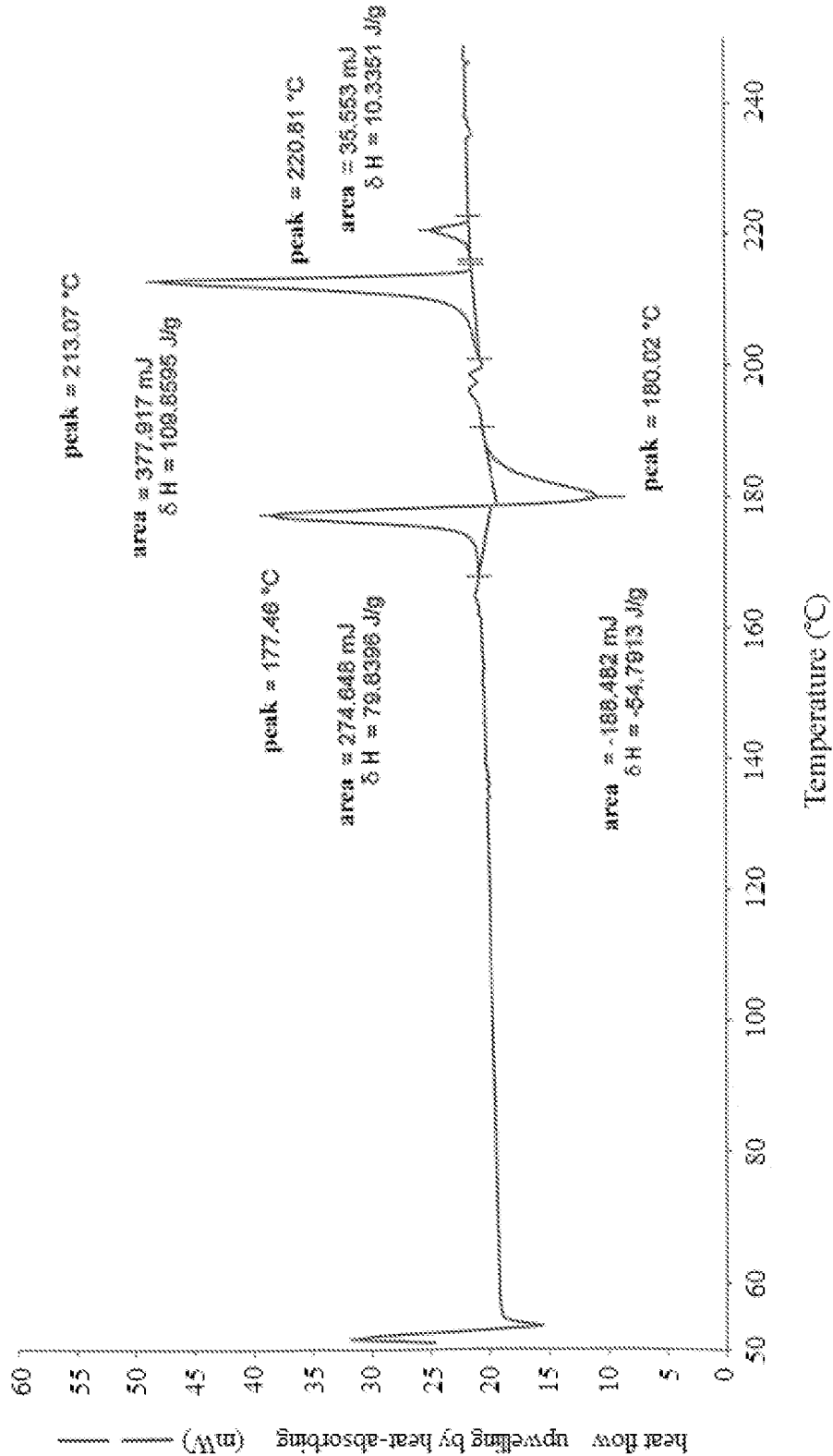
FIG. 4 is a differential scanning calorimetry curve of the non-solvated crystal A of the compound of formula (I) prepared in accordance with Example 1 of the present disclosure.

Preparation of Non-Solvated Crystal A of N-(2-aminophenyl)-6-(7-methoxyquinoline-4-oxo)-1-naphthaleneformamide 5.0 g of N-(2-aminophenyl)-6-(7-methoxyquinoline-4-oxo)-1-naphthaleneformamide was placed in a 2000 mL three-necked flask, and 750 mL of methanol was added. The mixture was heated with stirring in an oil bath at 65° C. until dissolved. The resulting solution was placed in a 0° C. ice water bath to cool and crystallize for 4 hours, filtered to collect the solid, and dried under vacuum at 80° C. for 12 hours to obtain non-solvated crystal A. As shown in FIG. 2, its X-ray powder diffraction pattern has characteristic peaks at reflection angles 2θ of about 4.42°, 6.88°, 8.78°, 9.26°, 12.74°, 13.82°, 15.78°, 18.58°, 20.86°, 22.56°, 25.72°, 27.08° and 28.72°; as shown in FIG. 3, its infrared spectrum has characteristic absorption peaks at about 3452, 3404, 3357, 3230, 3064, 1622, 1576, 1525, 1506, 1452, 1423, 1388, 1363, 1311, 1253, 1224, 1161, 1088 and 1024 $cm^{-1}$; as shown in FIG. 4, its differential scanning calorimetry curve has endothermic peaks at about 177.5° C., 213.1° C., and 220.8° C.; its proton nuclear magnetic resonance spectroscopy indicates that the crystal does not contain organic solvents.

EXAMPLE 2

Figure 5:
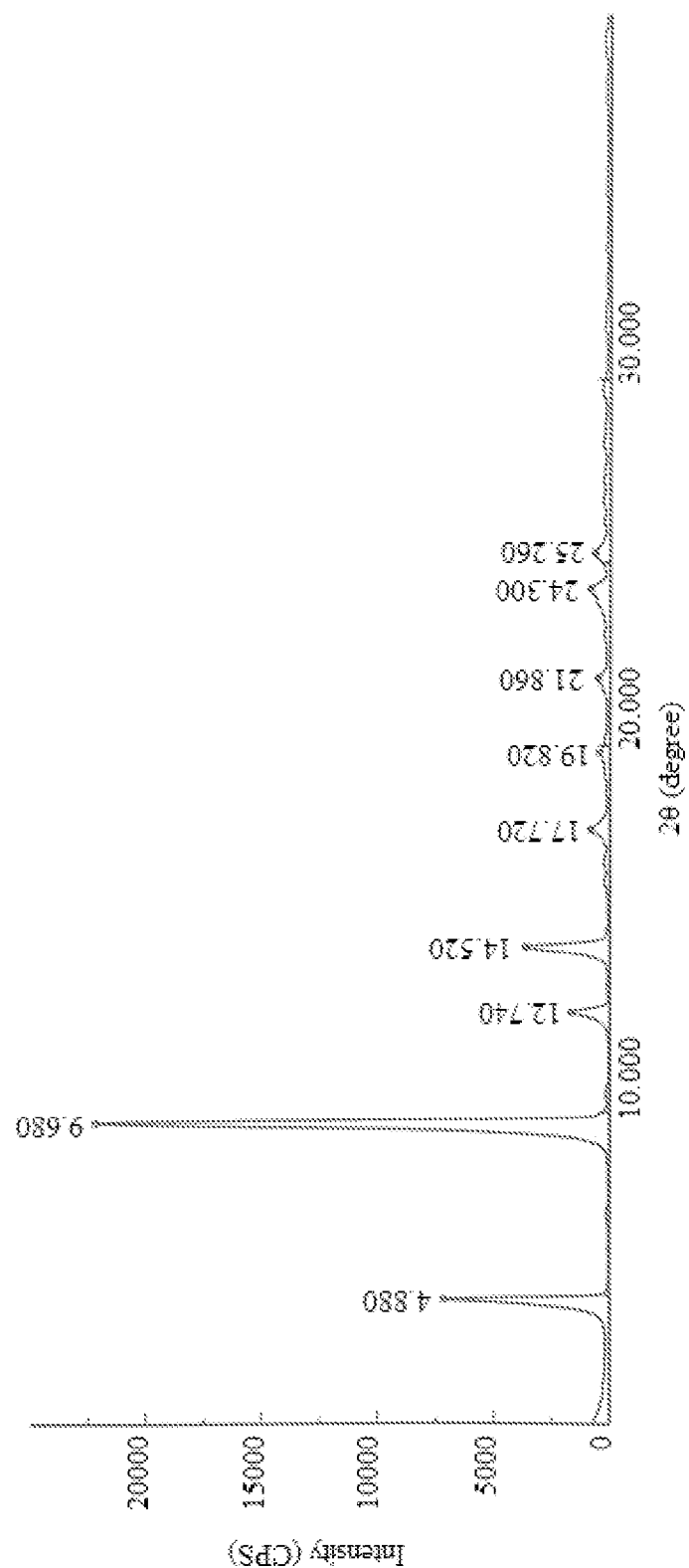
FIG. 5 is an X-ray powder diffraction pattern of the non-solvated crystal B of the compound of formula (I) prepared in accordance with Example 2 of the present disclosure.
Figure 6:
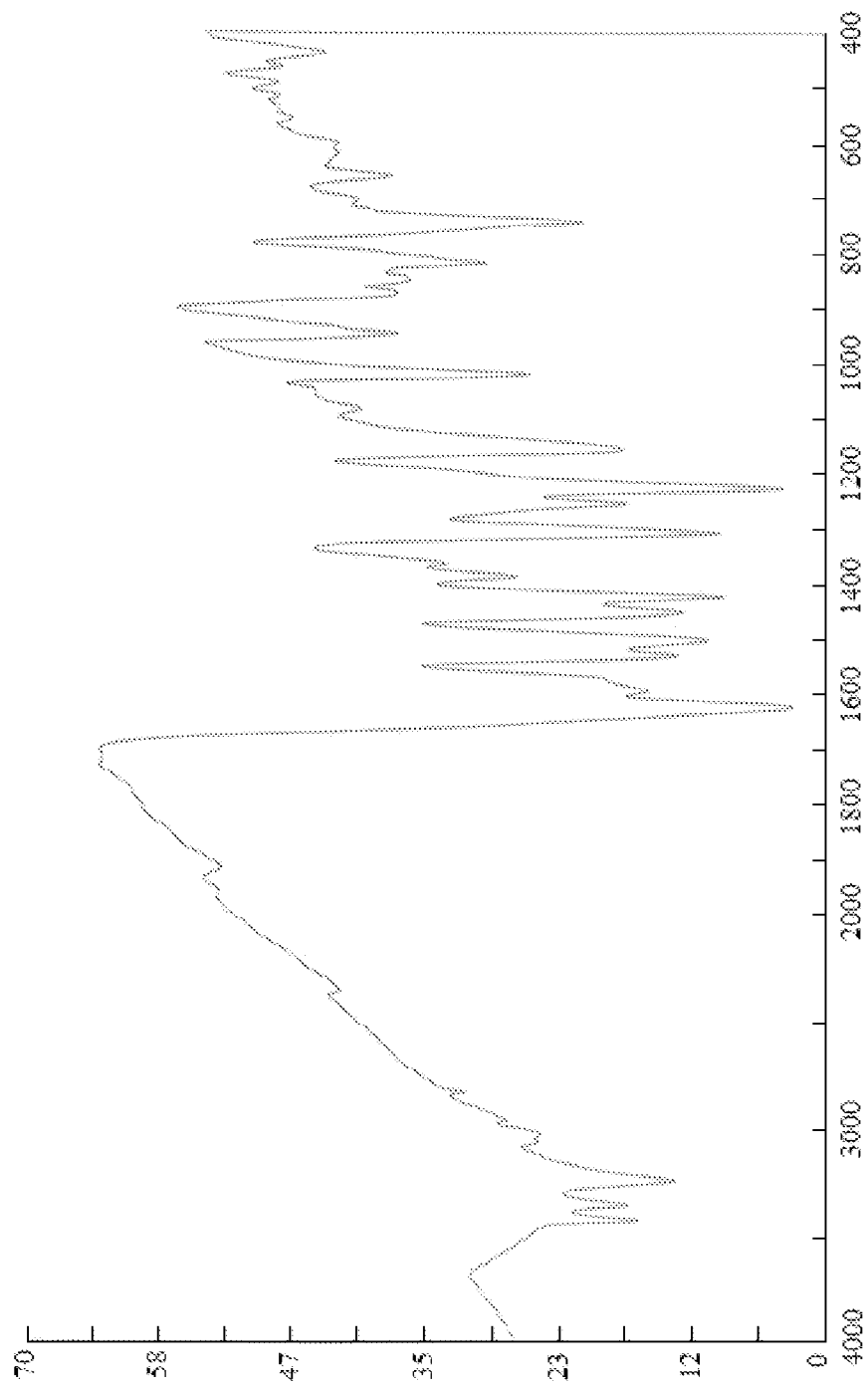
FIG. 6 is an infrared spectrum of the non-solvated crystal B of the compound of formula (I) prepared in accordance with Example 2 of the present disclosure.
Figure 7:
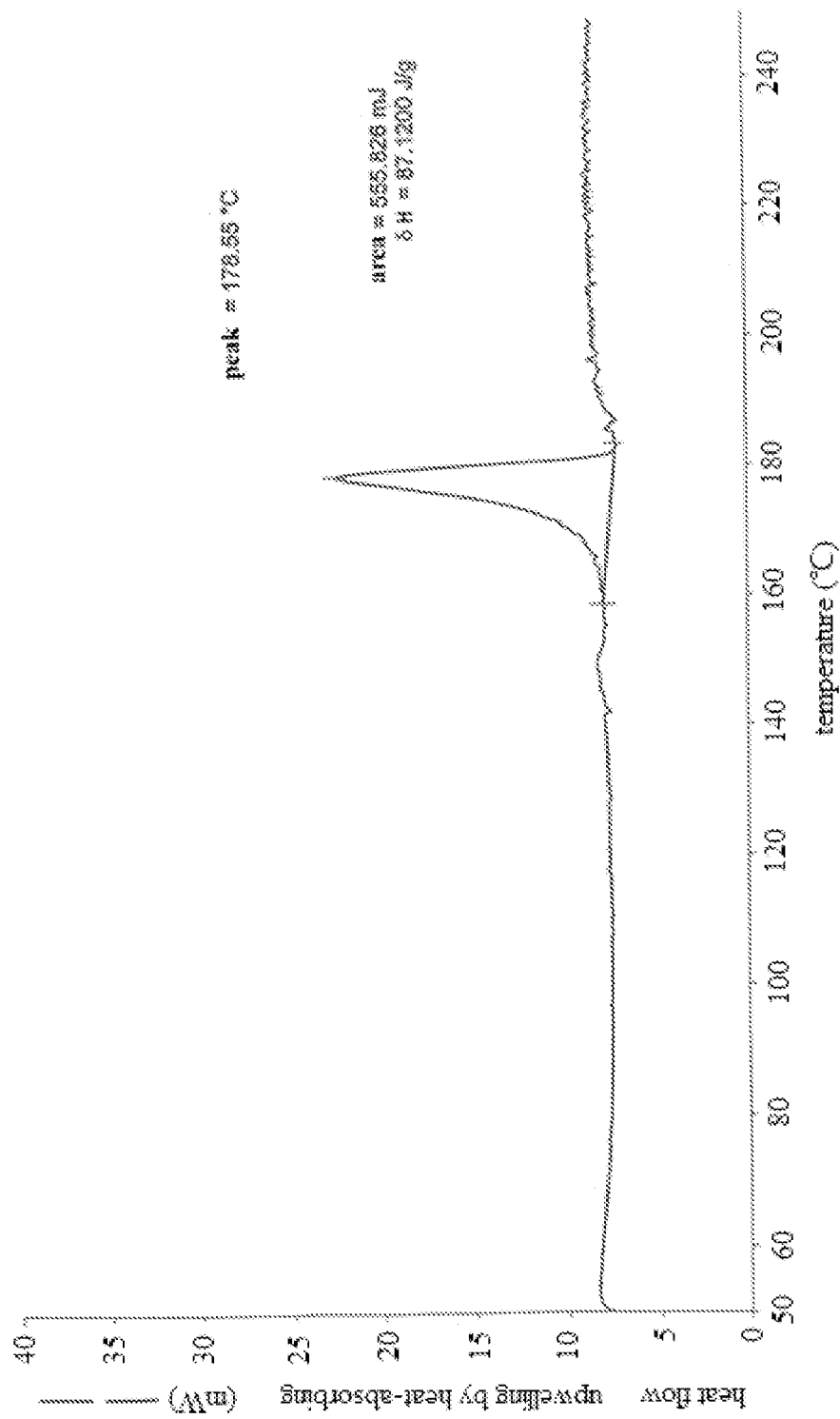
FIG. 7 is a differential scanning calorimetry curve of the non-solvated crystal B of the compound of formula (I) prepared in accordance with Example 2 of the present disclosure.

Preparation of Non-Solvated crystal B of N-(2-aminophenyl)-6-(7-methoxyquinoline-4-oxo)-1-naphthaleneformamide 5.0 g of N-(2-aminophenyl)-6-(7-methoxyquinoline-4-oxo)-1-naphthaleneformamide was placed in a 2000 mL three-necked flask, and 1000 mL of acetonitrile was added. The mixture was heated with stirring in an oil bath at 80° C. until dissolved. The resulting solution was placed in a 0° C. ice water bath to cool and crystallize for 4 hours, filtered to collect solid, and dried under vacuum at 80° C. for 12 hours to obtain non-solvated crystal B. As shown in FIG. 5, its X-ray powder diffraction pattern has characteristic peaks at reflection angles 2θ of about 4.88°, 9.68°, 12.74°, 14.52°, 17.72°, 19.82°, 21.86°, 24.30° and 25.26°; as shown in FIG. 6, its infrared spectrum has characteristic absorption peaks at about 3423, 3352, 3238, 3030, 1624, 1597, 1531, 1502, 1452, 1423, 1388, 1365, 1308, 1255, 1226, 1159, 1086 and 1022 $cm^{-1}$; as shown in FIG. 7, its differential scanning calorimetry curve has an endothermic peak at about 178.6° C.; its proton nuclear magnetic resonance spectroscopy indicates that the crystal does not contain organic solvents.

EXAMPLE 3

Figure 8:
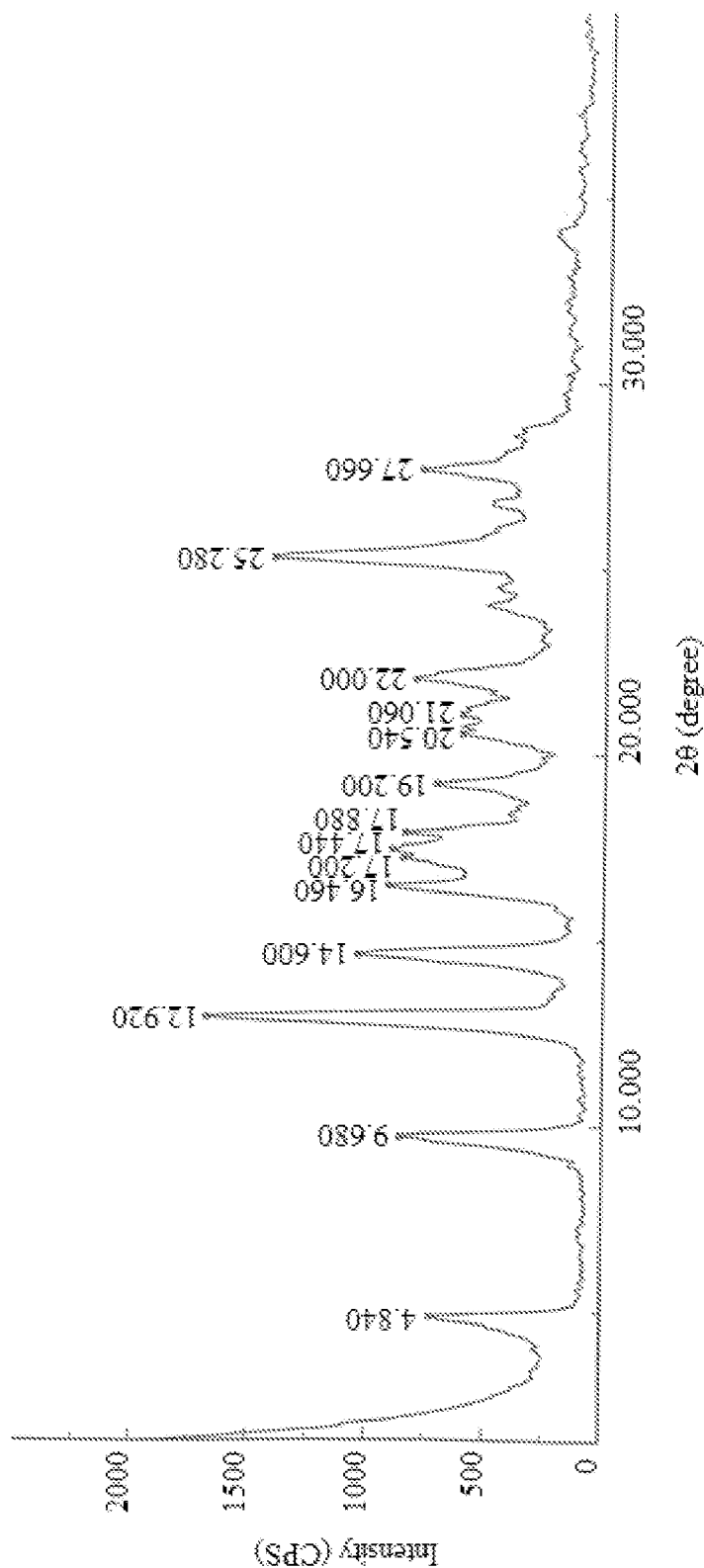
FIG. 8 is an X-ray powder diffraction pattern of the non-solvated crystal C of the compound of formula (I) prepared in accordance with Example 3 of the present disclosure.
Figure 9:
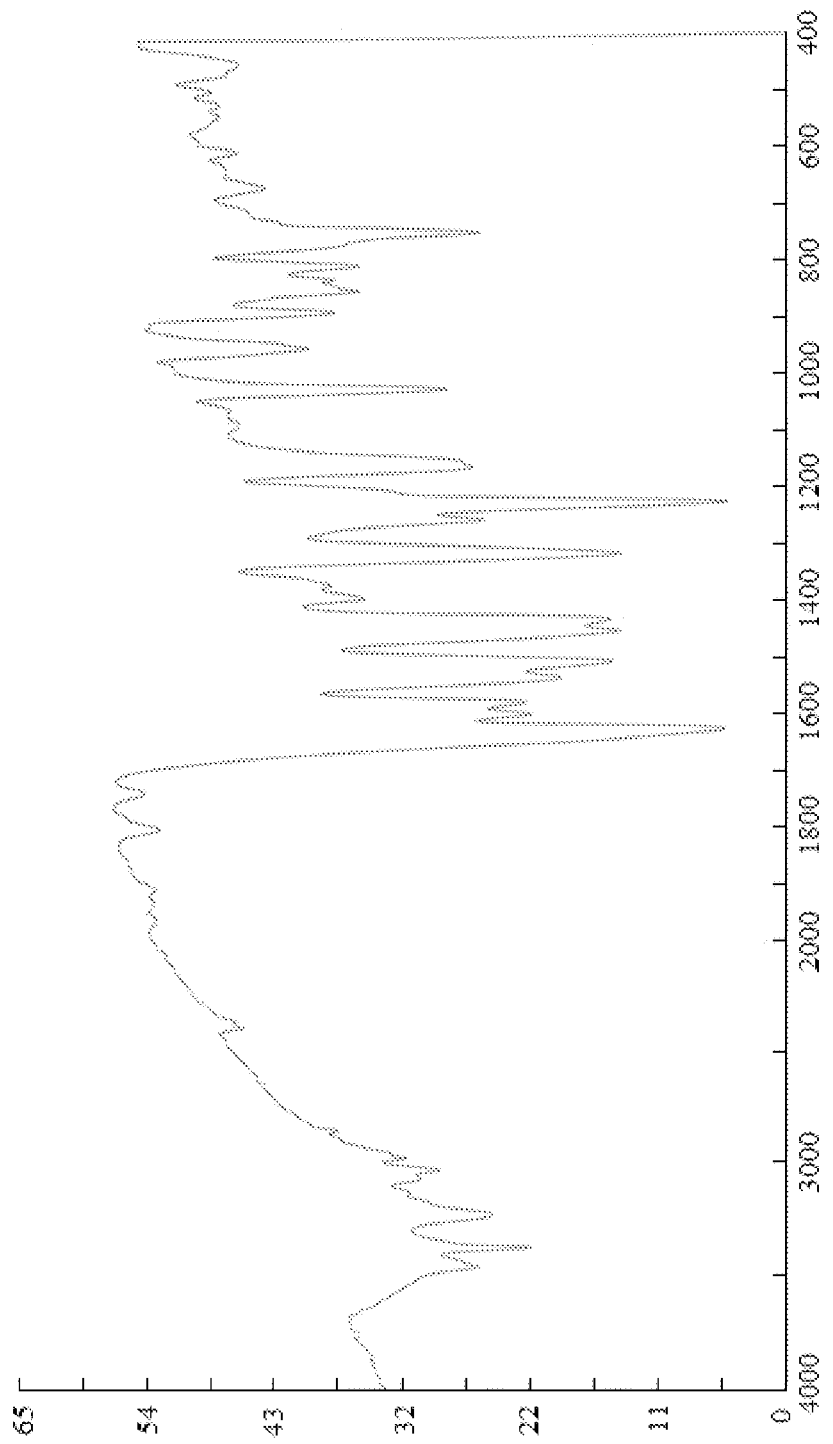
FIG. 9 is an infrared spectrum of the non-solvated crystal C of the compound of formula (I) prepared in accordance with Example 3 of the present disclosure.
Figure 10:
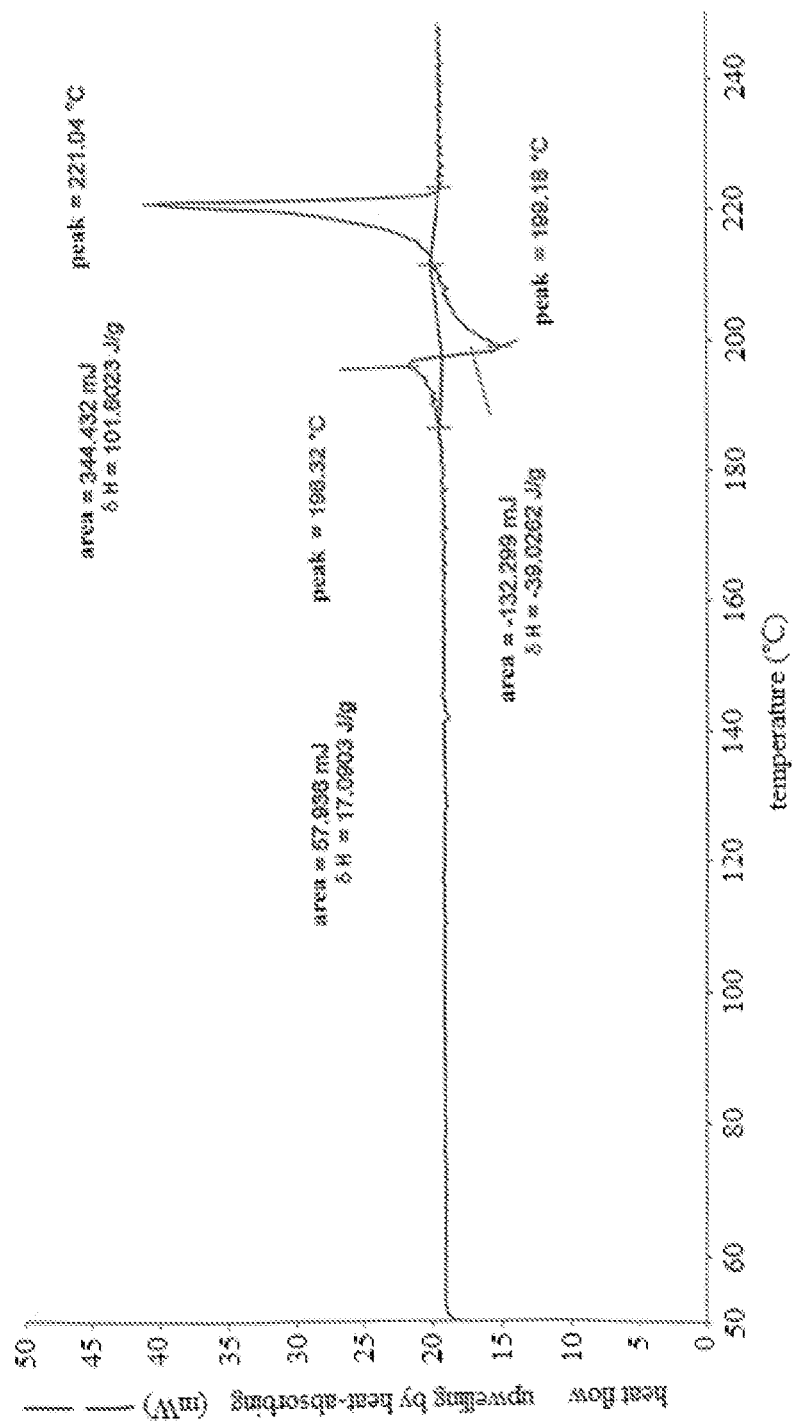
FIG. 10 is a differential scanning calorimetry curve of the non-solvated crystal C of the compound of formula (I) prepared in accordance with Example 3 of the present disclosure.

Preparation of Non-Solvated Crystal C of N-(2-aminophenyl)-6-(7-methoxyquinoline-4-oxo)-1-naphthaleneformamide 1.0 g of N-(2-aminophenyl)-6-(7-methoxyquinoline-4-oxo)-1-naphthaleneformamide was placed in a 50 mL three-necked flask, and 5 mL of dimethyl sulfoxide was added. The mixture was stirred at room temperature until dissolved. The resulting solution was added dropwise to 50 mL water under stirring and allowed to stand for 4 hours, filtered, washed with water, and the solid was collected and dried under vacuum at 80° C. for 24 hours to obtain a non-solvated crystal C. As shown in FIG. 8, its X-ray powder diffraction pattern has characteristic peaks at reflection angles 2θ of about 4.84°, 9.68°, 12.92°, 14.60°, 16.46°, 17.20°, 17.44°, 17.88°, 19.20°, 20.54°, 21.06°, 22.00°, 25.28° and 27.66°; as shown in FIG. 9, its infrared spectrum has characteristic absorption peaks at about 3452, 3369, 3217, 3016, 2962, 1793, 1728, 1626, 1595, 1574, 1531, 1502, 1448, 1429, 1388, 1311, 1252, 1224, 1159 and 1020 $cm^{-1}$; as shown in FIG. 10, its differential scanning calorimetry curve has endothermic peaks at about 196.3° C. and 221.0° C.; its proton nuclear magnetic resonance spectroscopy indicates that the crystal does not contain organic solvents.

EXAMPLE 4

Stability Test of the Crystal Form

High temperature (60° C.), high humidity (90%) and strong light irradiation (4500 Lx) tests of the non-solvated crystal A of example 1, non-solvated crystal B of example 2, and non-solvated crystal C of example 3 were performed according to the Chinese Pharmacopoeia 2010 edition, Part II, Appendix XIX C. Samples on day 0 and day 10 respectively were taken to determine the X-ray powder diffraction pattern and content (HPLC method). The test results showed that all three crystals remain unchanged in their original crystal forms, and the content of each crystal does not change significantly, indicating that the three crystals are all suitable for pharmaceutical manufacturing and long-term storage.

EXAMPLE 5

Preparation of Tablets of the Non-Solvated Crystal A of Example 1

Prescription (1000 tablets):

| | |
|---|---|
| Non-solvated crystal A of example 1 | 5 g |
| Microcrystalline cellulose | 90 g |
| Sodium carboxymethyl starch | 5 g |
| 4% Povidone K30 solution in ethanol | 50 g |
| Talc powder | 0.5 g |

Preparation process: Non-solvated crystal A of example 1 was pulverized and passed through a 100 mesh sieve, and microcrystalline cellulose, sodium carboxymethyl starch and talc powder were passed through an 80 mesh sieve. Prescribed amount of microcrystalline cellulose, sodium carboxymethyl starch and non-solvated crystal A were weighed and mixed uniformity. 4% povidone K30 solution in ethanol was added in an appropriate amount, and the mixture was granulated and dried. Prescribed amount of talcum powder was added, and the mixture was mixed uniformity and tableted to obtain the product.

EXAMPLE 6

Preparation of Capsules of the Non-Solvated Crystal A of Example 1

Prescription (1000 capsules):

| | |
|---|---|
| Non-solvated crystal A of example 1 | 5 g |
| Microcrystalline cellulose | 55 g |
| Lactose | 35 g |
| Sodium carboxymethyl starch | 5 g |
| Magnesium stearate | 0.5 g |

Preparation process: Non-solvated crystal A of example 1 was pulverized and passed through a 100 mesh sieve, and microcrystalline cellulose, lactose, sodium carboxymethyl starch and magnesium stearate were passed through an 80 mesh sieve. Prescribed amount of microcrystalline cellulose, lactose, sodium carboxymethyl starch, non-solvated crystal A and magnesium stearate were weighed and mixed uniformity. The mixture was filled into capsules to obtain the product.

EXAMPLE 7

Preparation of Tablets of the Non-Solvated Crystal B of Example 2

Prescription (1000 tablets):

| | |
|---|---|
| Non-solvated crystal B of example 2 | 5 g |
| Microcrystalline cellulose | 90 g |
| Sodium carboxymethyl starch | 5 g |
| 4% Povidone K30 solution in ethanol | 50 g |
| Talc powder | 0.5 g |

Preparation process: Non-solvated crystal B of example 2 was pulverized and passed through a 100 mesh sieve, and microcrystalline cellulose, sodium carboxymethyl starch and talc powder were passed through an 80 mesh sieve. Prescribed amount of microcrystalline cellulose, sodium carboxymethyl starch and non-solvated crystal B were weighed and mixed uniformity. 4% povidone K30 solution in ethanol was added in an appropriate amount, and the mixture was granulated and dried. Prescribed amount of talcum powder was added, and the mixture was mixed uniformity and tableted to obtain the product.

EXAMPLE 8

Preparation of Capsules of the Non-Solvated Crystal B of Example 2

Prescription (1000 capsules):

| | |
|---|---|
| Non-solvated crystal B of example 2 | 5 g |
| Microcrystalline cellulose | 55 g |
| Lactose | 35 g |
| Sodium carboxymethyl starch | 5 g |
| Magnesium stearate | 0.5 g |

Preparation process: Non-solvated crystal B of example 2 was pulverized and passed through a 100 mesh sieve, and microcrystalline cellulose, lactose, sodium carboxymethyl starch and magnesium stearate were passed through an 80 mesh sieve. Prescribed amount of microcrystalline cellulose, lactose, sodium carboxymethyl starch, non-solvated crystal B and magnesium stearate were weighed and mixed uniformity. The mixture was filled into capsules to obtain the product.

EXAMPLE 9

Preparation of Tablets of the Non-Solvated Crystal C of Example 3

Prescription (1000 tablets):

| | |
|---|---|
| Non-solvated crystal C of example 3 | 5 g |
| Microcrystalline cellulose | 90 g |
| Sodium carboxymethyl starch | 5 g |
| 4% Povidone K30 solution in ethanol | 50 g |
| Talc powder | 0.5 g |

Preparation process: Non-solvated crystal C of example 3 was pulverized and passed through a 100 mesh sieve, and microcrystalline cellulose, sodium carboxymethyl starch and talc powder were passed through an 80 mesh sieve. Prescribed amount of microcrystalline cellulose, sodium carboxymethyl starch and non-solvated crystal C were weighed and mixed uniformity. 4% povidone K30 solution in ethanol was added in an appropriate amount, and the mixture was granulated and dried. Prescribed amount of talcum powder was added, and the mixture was mixed uniformity and tableted to obtain the product.

EXAMPLE 10

Preparation of Capsules of the Non-Solvated Crystal C of Example 3

Prescription (1000 capsules):

| | |
|---|---|
| Non-solvated crystal C of example 3 | 5 g |
| Microcrystalline cellulose | 55 g |
| Lactose | 35 g |
| Sodium carboxymethyl starch | 5 g |
| Magnesium stearate | 0.5 g |

Preparation process: Non-solvated crystal C of example 3 was pulverized and passed through a 100 mesh sieve, and microcrystalline cellulose, lactose, sodium carboxymethyl starch and magnesium stearate were passed through an 80 mesh sieve. Prescribed amount of microcrystalline cellulose, lactose, sodium carboxymethyl starch, non-solvated crystal C and magnesium stearate were weighed and mixed uniformity. The mixture was filled into capsules to obtain the product.

The invention claimed is:

1. A non-solvated crystal of N-(2-aminophenyl)-6-(7-methoxyquinoline-4-oxo)-1-naphthaleneformamide, wherein said non-solvated crystal is selected from non-solvated crystal A, non-solvated crystal B, and non-solvated crystal C, wherein the X-ray powder diffraction pattern of said non-solvated crystal A has characteristic peaks at reflection angles 2θ of 6.88°, 9.26°, 12.74°, 13.82°, 18.58°, 20.86° and 25.72°;

the X-ray powder diffraction pattern of said non-solvated crystal B has characteristic peaks at reflection angles 2θ of 4.88°, 9.68°, 12.74°, 14.52°, 17.72°, 24.30° and 25.26°; and the X-ray powder diffraction pattern of said non-solvated crystal C has characteristic peaks at reflection angles 2θ of 4.84°, 9.68°, 12.92°, 14.60°, 16.46°, 17.44°, 22.00° and 25.28°.

2. The non-solvated crystal according to claim 1, wherein the X-ray powder diffraction pattern of said non-solvated crystal A has characteristic peaks at reflection angles 2θ of 4.42°, 6.88°, 8.78°, 9.26°, 12.74°, 13.82°, 18.58°, 20.86° and 25.72°.

3. The non-solvated crystal according to claim 1, wherein the infrared spectrum of the non-solvated crystal A has characteristic absorption peaks at 3452, 3404, 3357, 3230, 3064, 1622, 1576, 1525, 1506, 1452, 1423, 1388, 1363, 1311, 1253, 1224, 1161, 1088 and 1024 cm$^{-1}$; and/or its differential scanning calorimetry curve has endothermic peaks at 177.5° C., 213.1° C., and 220.8° C.

4. The non-solvated crystal according to claim 1, wherein the X-ray powder diffraction pattern of said non-solvated crystal B has characteristic peaks at reflection angles 2θ of 4.88°, 9.68°, 12.74°, 14.52°, 17.72°, 19.82°, 21.86°, 24.30° and 25.26°.

5. The non-solvated crystal according to claim 1, wherein the infrared spectrum of the non-solvated crystal B has characteristic absorption peaks at 3423, 3352, 3238, 3030, 1624, 1597, 1531, 1502, 1452, 1423, 1388, 1365, 1308, 1255, 1226, 1159, 1086 and 1022 cm$^{-1}$; and/or its differential scanning calorimetry curve has an endothermic peak at 178.6° C.

6. The non-solvated crystal according to claim 1, wherein the X-ray powder diffraction pattern of said non-solvated crystal C has characteristic peaks at reflection angles 2θ of 4.84°, 9.68°, 12.92°, 14.60°, 16.46°, 17.44°, 17.88°, 22.00°, 25.28° and 27.66°.

7. The non-solvated crystal according to claim 1, wherein the infrared spectrum of the non-solvated crystal C has characteristic absorption peaks at 3452, 3369, 3217, 3016, 2962, 1793, 1728, 1626, 1595, 1574, 1531, 1502, 1448, 1429, 1388, 1311, 1252, 1224, 1159 and 1020 cm$^{-1}$; and/or its differential scanning calorimetry curve has endothermic peaks at 196.3° C. and 221.0° C.

8. A method for preparing the non-solvated crystal A of N-(2-aminophenyl)-6-(7-methoxyquinoline-4-oxo)-1-naphthaleneformamide according to claim 2, comprising the steps of: adding N-(2-aminophenyl)-6-(7-methoxyquinoline-4-oxo)-1-naphthaleneformamide to methanol, heating at 65° C. until dissolved and cooling at 0° C. to precipitate.

9. A method for preparing the non-solvated crystal B of N-(2-aminophenyl)-6-(7-methoxyquinoline-4-oxo)-1-naphthaleneformamide according to claim 4, comprising the steps of: adding N-(2-aminophenyl)-6-(7-methoxyquinoline-4-oxo)-1-naphthaleneformamide to acetonitrile, heating at 80° C. until dissolved and cooling at 0° C. to precipitate.

10. A method for preparing the non-solvated crystal C of N-(2-aminophenyl)-6-(7-methoxyquinoline-4-oxo)-1-naphthaleneformamide according to claim 6, comprising the steps of: adding N-(2-aminophenyl)-6-(7-methoxyquinoline-4-oxo)-1-naphthaleneformamide to dimethyl sulfoxide, stirring at room temperature until dissolved, adding dropwise the resulting solution to water under stirring, and filtering to collect solid.

11. A pharmaceutical composition comprising the non-solvated crystal of N-(2-aminophenyl)-6-(7-methoxyquinoline-4-oxo)-1-naphthaleneformamide according to claim 1.

12. The non-solvated crystal according to claim 2, wherein the X-ray powder diffraction pattern of said non-solvated crystal A has characteristic peaks at reflection angles 2θ of 4.42°, 6.88°, 8.78°, 9.26°, 12.74°, 13.82°, 15.78°, 18.58°, 20.86°, 22.56°, 25.72°, 27.08° and 28.72°.

13. The non-solvated crystal according to claim 2, wherein the X-ray powder diffraction pattern of said non-solvated crystal A is shown in FIG. 2.

14. The non-solvated crystal according to claim 4, wherein the X-ray powder diffraction pattern of said non-solvated crystal B is shown in FIG. 5.

15. The non-solvated crystal according to claim 6, wherein the X-ray powder diffraction pattern of said non-solvated crystal C has characteristic peaks at reflection angles 2θ of 4.84°, 9.68°, 12.92°, 14.60°, 16.46°, 17.44°, 17.88°, 19.20°, 20.54°, 21.06°, 22.00°, 25.28° and 27.66°.

16. The non-solvated crystal according to claim 6, wherein the X-ray powder diffraction pattern of said non-solvated crystal C is shown in FIG. 8.

* * * * *